(12) United States Patent  (10) Patent No.: US 7,888,383 B2
Sandham  (45) Date of Patent: Feb. 15, 2011

(54) ORGANIC COMPOUNDS

(75) Inventor: David Andrew Sandham, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/096,332

(22) PCT Filed: Dec. 7, 2006

(86) PCT No.: PCT/EP2006/011771

§ 371 (c)(1),
(2), (4) Date: Mar. 3, 2009

(87) PCT Pub. No.: WO2007/065684

PCT Pub. Date: Jun. 14, 2007

(65) Prior Publication Data

US 2009/0221578 A1 Sep. 3, 2009

(30) Foreign Application Priority Data

Dec. 9, 2005 (GB) .................................. 0525141.8

(51) Int. Cl.
*C07D 413/12* (2006.01)
*C07D 403/12* (2006.01)
*C07D 209/22* (2006.01)
*A61K 31/5377* (2006.01)
*A61K 31/405* (2006.01)

(52) U.S. Cl. ............... 514/419; 514/235.2; 514/210.21; 514/414; 544/143; 548/465; 548/494

(58) Field of Classification Search ............... 548/465, 548/494; 544/143; 514/419, 235.2

See application file for complete search history.

(56) References Cited

U.S. PATENT DOCUMENTS 6,500,853 B1 12/2002 Seehra et al.
2009/0155903 A1 * 6/2009 Slade et al. .................. 435/375

FOREIGN PATENT DOCUMENTS

EP           1600440 A1 *  11/2005
WO         WO99/43654 A2    9/1999
WO        WO2005/040112 A1   5/2005
WO        WO 2005040112 A1 *  5/2005

OTHER PUBLICATIONS

Berge et al. J. Pharm. Sci. 1997, 66, pp. 1-19.*

* cited by examiner

*Primary Examiner*—Rebecca L Anderson
*Assistant Examiner*—Matthew P Coughlin
(74) *Attorney, Agent, or Firm*—Paul D. Strain, Esq.; Fanelli Strain & Haag PLLC

(57) ABSTRACT

There are provided according to the invention compounds of formula (I)

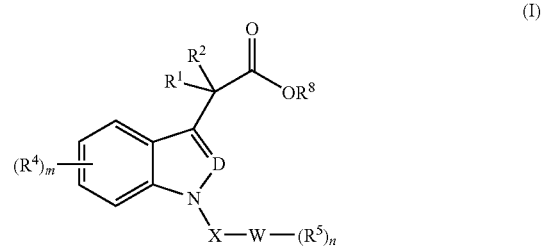

in free or salt form, wherein
$R^1$, $R^2$, $R^4$, $R^5$, $R^6$, D, X, W, m and n are as described in the specification, process for preparing them, and their use as pharmaceuticals.

2 Claims, No Drawings

ORGANIC COMPOUNDS

This application is a U.S. National Phase filing of PCT/EP2006/011771 filed 7 Dec. 2006, and claims priority to GB Patent Application 0525141.8 filed 9 Dec. 2005, the contents of which are incorporated herein by reference in their entirety.

The present invention relates to organic compounds, their preparation and their use as pharmaceuticals.

In a first aspect, the present invention provides compounds of formula (I)

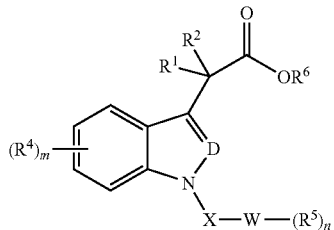

in free or salt form, wherein

D is selected independently from $CR^3$ and N;

$R^1$ and $R^2$ are, independently, H, halogen or $C_1$-$C_8$-alkyl, or $R^1$ and $R^2$, together with the carbon atom to which they are attached, form a $C_3$-$C_{15}$-carbocyclic group;

$R^3$ is selected from $C_1$-$C_8$-alkyl, halogen, cyano, hydroxyl, amino, aminoalkyl, amino(di)alkyl, a $C_3$-$C_{15}$-carbocyclic group, $C_1$-$C_8$-haloalkyl, $C_1$-$C_8$alkoxy-$C_1$-$C_8$-alkyl, and $C_1$-$C_8$-hydroxyalkyl;

each $R^4$ is independently selected from halogen, $C_1$-$C_8$-alkyl, $C_1$-$C_8$-haloalkyl, a $C_3$-$C_{15}$-carbocyclic group, $C_6$-$C_{15}$-aromatic carbocyclic group, nitro, cyano, $C_1$-$C_8$-alkylsulfonyl, $C_1$-$C_8$-alkylsulfinyl, $C_1$-$C_8$-alkylcarbonyl, $C_1$-$C_8$-alkoxycarbonyl, $C_1$-$C_8$-alkoxy, $C_1$-$C_8$-haloalkoxy, carboxy, carboxy-$C_1$-$C_8$-alkyl, amino, $C_1$-$C_8$-alkylamino, di($C_1$-$C_8$-alkyl)amino, $SO_2NH_2$, ($C_1$-$C_8$-alkylamino)sulfonyl, di($C_1$-$C_8$-alkyl)aminosulfonyl, aminocarbonyl, $C_1$-$C_8$-alkylaminocarbonyl, di($C_1$-$C_8$-alkyl)aminocarbonyl and a 4- to 10-membered heterocyclic group;

each $R^5$ is independently selected from $C_1$-$C_8$-haloalkyl, —$SO_2$—$C_1$-$C_8$-alkyl, —$SO_2$—$C_1$-$C_8$-haloalkyl, or 4- to 14-membered heterocyclic,

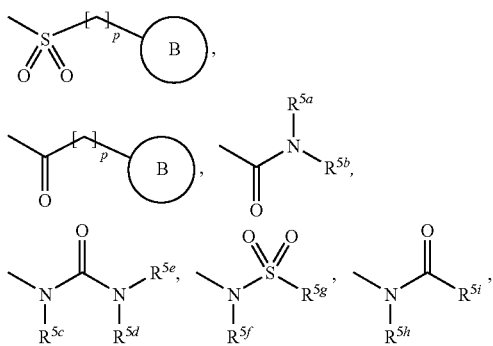

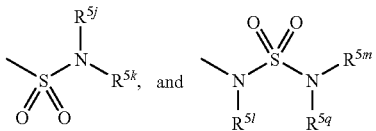

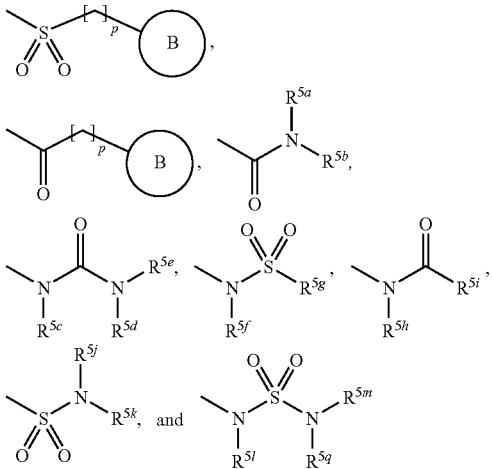

when n is an integer from 2-3, or $R^5$ is independently selected from when n is 1;

$R^{5a}$ and $R^{5b}$ are independently selected from H, a 4- to 14-membered heterocyclic group, a $C_6$-$C_{15}$-aromatic carbocyclic group, a $C_3$-$C_{15}$-carbocyclic group, and $C_1$-$C_8$-alkyl optionally substituted by 4- to 14-membered heterocyclic group or $C_3$-$C_{15}$-carbocyclic group where at least one of $R^{5a}$ or $R^{5b}$ is $C_1$-$C_8$-alkyl substituted by a 4- to 14-membered heterocyclic group or $C_3$-$C_{15}$-carbocyclic group, or $R^{5a}$ and $R^{5b}$ together with the nitrogen atom to which they are attached form a 4- to 14-membered heterocyclic group, $R^5$, $R^{5d}$ and $R^{5e}$ are independently selected from H, and $C_1$-$C_8$-alkyl optionally substituted by a 4- to 14-membered heterocyclic group, a $C_6$-$C_{15}$-aromatic carbocyclic group, or a $C_3$-$C_{15}$-carbocyclic group, or $R^{5c}$ along with $R^{5d}$ or $R^{5e}$ together with the nitrogen atoms to which they are attached and the carbonyl form a 5- to 14-membered heterocyclic group;

$R^{5f}$ is H, $C_1$-$C_8$-alkyl optionally substituted by a 4- to 14-membered heterocyclic group or $C_3$-$C_{15}$-carbocyclic group;

$R^{5g}$ is selected from H, and $C_1$-$C_8$-alkyl optionally substituted by a 4- to 14-membered heterocyclic group or $C_3$-$C_{15}$-carbocyclic group;

$R^{5f}$ and $R^{5g}$ together with the $NSO_2$ group to which they are attached form a 5- to 14-membered heterocyclic group;

$R^{5h}$ and $R^{5i}$ are independently selected from H, and $C_1$-$C_8$-alkyl optionally substituted by a 4- to 14-membered heterocyclic group or $C_3$-$C_{15}$-carbocyclic group, or $R^{5h}$ and $R^{5i}$ together with the NCO group to which they are attached form a 5- to 14-membered heterocycle;

$R^{5j}$ and $R^{5k}$ are independently selected from H, and $C_1$-$C_8$-alkyl optionally substituted by a 4- to 14-membered heterocyclic group or $C_3$-$C_{15}$-carbocyclic group, or $R^{5j}$ and $R^{5k}$ together with the nitrogen atom to which they are attached form a 4- to 14-membered heterocyclic group;

$R^{5l}$, $R^{5m}$ and $R^{5q}$ are independently selected from H, and $C_1$-$C_8$-alkyl optionally substituted by a 4- to 14-membered heterocyclic group or $C_3$-$C_{15}$-carbocyclic group, or $R^{5l}$ along with $R^{5m}$ or $R^{5q}$ together with the nitrogen atoms of the aminosulfonamide to which they are attached form a 5- to 14-membered heterocyclic group;

B is selected from 4- to 14-membered heterocyclic group, a $C_6$-$C_{15}$-aromatic carbocyclic group, and a $C_3$-$C_{15}$-carbocyclic group;

$R^6$ is H or $C_1$-$C_8$-alkyl optionally substituted by $C_3$-$C_{15}$-carbocyclic group, or a $C_3$-$C_{15}$-carbocyclic group;

W is a $C_6$-$C_{15}$-aromatic carbocyclic group or a 4- to 14-membered heterocyclic group, with the proviso that W is not benzothiazole;

X is a bond, $C_1$-$C_8$-alkyl optionally substituted by one or more groups selected from $C_1$-$C_8$-alkyl, halo-$C_1$-$C_8$-alky, halo, oxo, hydroxyl, amino, aminoalkyl; and amino (dialkyl), $(V_1)$-T-(V), a 4- to 14-membered heterocyclic group, a $C_6$-$C_{15}$-aromatic carbocyclic group, —$SO_2$—, —$CONR^7(C_1$-$C_8$-alkyl)-, or a $C_3$-$C_{15}$-carbocyclic group;

$V_1$ is $C_1$-$C_7$-alkyl optionally substituted by $C_1$-$C_8$ alkyl, halo, oxo, hydroxyl, amino, amino-$C_1$-$C_8$-alkyl, amino (di-$C_1$-$C_8$-alkyl);

V is $C_0$-$C_7$-alkyl optionally substituted by $C_1$-$C_8$ alkyl, halo, oxo, hydroxyl, amino, amino-$C_1$-$C_8$-alkyl, amino (di-$C_1$-$C_8$-alkyl);

T is oxygen or $NR^7$;

$R^7$ is H or $C_1$-$C_8$-alkyl;

wherein each $C_3$-$C_{15}$-carbocyclic group, $C_6$-$C_{15}$-membered aromatic carbocyclic group and each 4- to 14-membered heterocyclic group, unless otherwise specified is independently optionally substituted by one or more groups selected from halo, oxo, hydroxy, cyano, amino, nitro, carboxy, $C_1$-$C_8$-alkyl, halo-$C_1$-$C_8$-alkyl, $C_1$-$C_8$-alkoxy, $C_1$-$C_8$-alkylcarbonyl, $C_1$-$C_8$-alkylsulfonyl, —$SO_2NH_2$, ($C_1$-$C_8$-alkylamino)-sulfonyl, di($C_1$-$C_8$-alkyl)aminosulfonyl, aminocarbonyl, $C_1$-$C_8$-alkylaminocarbonyl and di($C_1$-$C_8$-alkyl)aminocarbonyl, a $C_3$-$C_{15}$-carbocyclic group, a $C_6$-$C_{15}$ aromatic carbocyclic group, a 4- to 14-membered heterocyclic group, cyano-$C_1$-$C_8$-alkyl, hydroxy-$C_1$-$C_8$-alkyl, $C_1$-$C_8$-haloalkyl, amino-$C_1$-$C_8$-alkyl, amino(hydroxy)$C_1$-$C_8$-alkyl and $C_1$-$C_8$-alkoxy optionally substituted by aminocarbonyl;

m is an integer from 0-3;

n is an integer from 1-3; and p is an integer from 0-4.

According to formula (I), the compounds of formula (I) are suitably

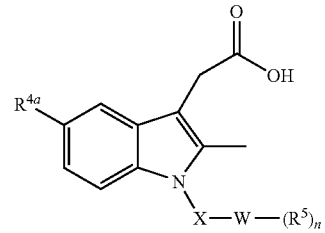

(I)

in free or salt form, $R^{4a}$ is H or halogen.

X is —$CH_2$—.

According to formula (I), W is a $C_6$-$C_{15}$ aromatic carbocyclic group, e.g. phenyl. Where W is phenyl, it is suitably 2,4-substituted by $R^5$.

According to formula (I) each $R^5$ is independently suitably selected from $C_1$-$C_8$-haloalkyl, preferably trifluoromethyl, and —$SO_2$—$C_1$-$C_8$-alkyl, preferably —$SO_2$—$CH_3$.

According to formula (I), $R^5$ is suitably

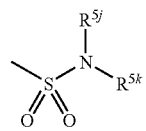

where $R^{5j}$ and $R^{5k}$ together with the nitrogen atom to which they are attached form a 4- to 6-membered heterocyclic group, i.e. piperazine, azetidine, morpholine, piperidine, and pyrrolidine. The 4- to 6-membered heterocyclic group can be optionally substituted by $C_1$-$C_8$-alkyl, preferably methyl, or $R^{5j}$ and $R^{5k}$ are independently selected from $C_1$-$C_8$-alkyl, preferably methyl or a $C_3$-$C_{15}$-carbocyclic group, such as cyclohexane, when n is 1.

According to formula (I), when n is an integer from 2-3, each $R^5$ is independently suitably

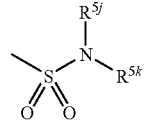

where $R^{5j}$ and $R^{5k}$ together with the nitrogen atom to which they are attached form a 4- to 6-membered heterocyclic group, i.e. piperazine, azetidine, morpholine, piperidine, and pyrrolidine. The 4- to 6-membered heterocyclic group can be optionally substituted by $C_1$-$C_8$-alkyl, preferably methyl, or $R^{5j}$ and $R^{5k}$ are independently selected from $C_1$-$C_8$-alkyl, preferably methyl or a $C_3$-$C_{15}$-carbocyclic group, such as cyclohexane.

A more preferred embodiment of the present invention provides compounds of formula (Ia)

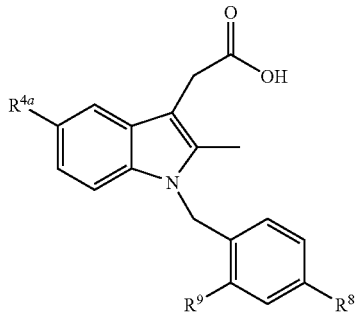

where
R$^{4a}$ is H or fluorine;
R$^9$ is H or C$_1$-C$_8$-haloalkyl; and
R$^8$ is selected from —SO$_2$—C$_1$-C$_8$-alkyl,

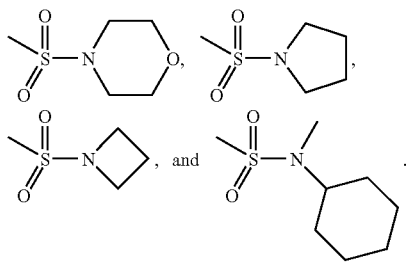

Terms used in the specification have the following meanings:

"Optionally substituted", as used herein, means the group referred to can be substituted at one or more positions by any one or any combination of the radicals listed thereafter.

"Halogen" or "halo" may be fluorine, chlorine, bromine or iodine.

"C$_1$-C$_8$-alkyl" denotes straight-chain or branched C$_1$-C$_8$-alkyl, which may be, e.g., methyl, ethyl, n-propyl, isopropyl, n-butyl, isobutyl, sec-butyl, tert-butyl, straight- or branched-pentyl, straight- or branched-hexyl, straight- or branched-heptyl or straight- or branched-octyl.

"C$_3$-C$_{15}$-carbocyclic group", as used herein, denotes a carbocyclic group having 3- to 15-ring carbon atoms that is saturated or partially saturated, such as a C$_3$-C$_8$-cycloalkyl. Examples of C$_3$-C$_{15}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and indenyl, and bicyclodecyl.

"C$_6$-C$_{15}$-aromatic carbocyclic group", as used herein, denotes an aromatic group having 6- to 15-ring carbon atoms. Examples of C$_6$-C$_{15}$-Aromatic carbocyclic groups include but are not limited to phenyl, phenylene, benzenetriyl, naphthyl, naphthylene, naphthalenetriyl or anthrylene.

"C$_1$-C$_8$-alkoxy" denotes straight-chain or branched C$_1$-C$_8$-alkoxy which may be, e.g., methoxy, ethoxy, n-propoxy, iso-propoxy, n-butoxy, isobutoxy, sec-butoxy, tert-butoxy, straight- or branched-pentoxy, straight- or branched-hexyloxy, straight- or branched-heptyloxy or straight- or branched-octyloxy. Preferably, C$_1$-C$_8$-alkoxy is C$_1$-C$_4$-alkoxy.

"C$_1$-C$_8$-haloalkyl" and "C$_1$-C$_8$-haloalkoxy" denote C$_1$-C$_8$-alkyl and C$_1$-C$_8$-alkoxy as hereinbefore defined substituted by one or more halogen atoms, preferably one, two or three halogen atoms, preferably fluorine, bromine or chlorine atoms. Preferably, C$_1$-C$_8$-haloalkyl is C$_1$-C$_4$-alkyl substituted by one, two or three fluorine, bromine or chlorine atoms.

"C$_1$-C$_8$-alkylsulfonyl", as used herein, denotes C$_1$-C$_8$-alkyl as hereinbefore defined linked to —SO$_2$—.

"C$_1$-C$_8$-alkylsulfinyl", as used herein, denotes C$_1$-C$_8$-alkyl as hereinbefore defined linked to —SO—.

"Amino-C$_1$-C$_8$-alkyl" and "amino-C$_1$-C$_8$-alkoxy" denote amino attached by a nitrogen atom to C$_1$-C$_8$-alkyl, e.g., NH$_2$—(C$_1$-C$_8$)—, or to C$_1$-C$_8$-alkoxy, e.g., NH$_2$—(C$_1$-C$_8$)—O—, respectively, as hereinbefore defined.

"Amino-(hydroxy)-C$_1$-C$_8$-alkyl" denotes amino attached by a nitrogen atom to C$_1$-C$_8$-alkyl and hydroxy attached by an oxygen atom to the same C$_1$-C$_8$-alkyl.

"Carboxy-C$_1$-C$_8$-alkyl" and "carboxy-C$_1$-C$_8$-alkoxy" denote carboxy attached by a carbon atom to C$_1$-C$_8$-alkyl or C$_1$-C$_8$-alkoxy, respectively, as hereinbefore defined.

"C$_1$-C$_8$-alkylcarbonyl", "C$_1$-C$_8$-alkoxycarbonyl" and "C$_1$-C$_8$-haloalkylcarbonyl" denote C$_1$-C$_8$-alkyl, C$_1$-C$_8$-alkoxy or C$_1$-C$_8$-haloalkyl, respectively, as hereinbefore defined attached by a carbon atom to a carbonyl group. "C$_1$-C$_8$-alkoxycarbonyl" denotes C$_1$-C$_8$-alkoxy as hereinbefore defined wherein the oxygen of the alkoxy group is attached to the carbonyl carbon.

"C$_1$-C$_8$-alkylamino" and "di(C$_1$-C$_8$-alkyl)amino" denote C$_1$-C$_8$-alkyl as hereinbefore defined attached by a carbon atom to an amino group. The C$_1$-C$_8$-alkyl groups in di(C$_1$-C$_8$-alkyl)amino may be the same or different.

"C$_1$-C$_8$-alkylaminocarbonyl" and "di(C$_1$-C$_8$-alkyl)aminocarbonyl" denote C$_1$-C$_8$-alkylamino and di(C$_1$-C$_8$-alkyl)amino, respectively, as hereinbefore defined attached by a nitrogen atom to the carbon atom of a carbonyl group.

"Di(C$_1$-C$_8$-alkyl)amino-C$_1$-C$_8$-alkyl" and "di(C$_1$-C$_8$-alkyl)amino-C$_1$-C$_8$-alkoxy" denote di(C$_1$-C$_8$-alkyl)amino as hereinbefore defined attached by a nitrogen atom to the carbon atom of a C$_1$-C$_8$-alkyl or a C$_1$-C$_8$-alkoxy group, respectively.

"4- to 14-membered heterocyclic group", refers to a 4- to 14-membered heterocyclic ring containing at least one ring heteroatom selected from the group consisting of nitrogen, oxygen and sulphur, which may be saturated, partially saturated or unsaturated (aromatic). Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indazole, indole or thiazole. The 4- to 14-membered heterocyclic group can be unsubstituted or substituted. Preferred substituents include halo, cyano, oxo, hydroxy, carboxy, nitro, C$_1$-C$_8$-alkyl, C$_1$-C$_8$-alkylcarbonyl, cyano-C$_1$-C$_8$-alkyl, hydroxy-C$_1$-C$_8$-alkyl, C$_1$-C$_8$-haloalkyl, amino-C$_1$-C$_8$-alkyl, amino(hydroxy)C$_1$-C$_8$-alkyl and C$_1$-C$_8$-alkoxy optionally substituted by aminocarbonyl. Especially preferred substituents include halo, oxo, C$_1$-C$_4$-alkyl, C$_1$-C$_4$-alkylcarbonyl, hydroxy-C$_1$-C$_4$-alkyl, C$_1$-C$_4$-haloalkyl, amino-C$_1$-C$_4$-alkyl and amino(hydroxy)C$_1$-C$_4$-alkyl.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Where in formula (I), m or n are 2, the two substituents may be the same or different. Where m or n are 3, two or all of the substituents may be the same, or all three may be different.

In a yet further aspect, the present invention provides for the use of a compound of formula (I) in any of the aforementioned embodiments, in free or salt form, for the manufacture of a medicament for the treatment of an inflammatory or allergic condition, particularly an inflammatory or obstructive airways disease.

Salts and Isomers

Many of the compounds represented by formula (I) are capable of forming acid addition salts, particularly pharmaceutically acceptable acid addition salts. Pharmaceutically acceptable acid addition salts of the compound of formula (I) include those of inorganic acids, e.g., hydrohalic acids, such as hydrochloric acid or hydrobromic acid; nitric acid; sulphuric acid; phosphoric acid; and organic acids, e.g., aliphatic monocarboxylic acids, such as formic acid, acetic acid, diphenylacetic acid, triphenylacetic acid, caprylic acid, dichloroacetic acid, trifluoroacetic acid, hippuric acid, propionic acid and butyric acid; aliphatic hydroxy acids, such as lactic acid, citric acid, gluconic acid, mandelic acid, tartaric acid or malic acid; dicarboxylic acids, such as adipic acid, aspartic acid, fumaric acid, glutamic acid, maleic add, malonic acid, sebacic acid or succinic acid; aromatic carboxylic acids, such as benzoic acid, p-chlorobenzoic acid, or nicotinic acid; aromatic hydroxy acids, such as o-hydroxybenzoic acid, p-hydroxybenzoic acid, 1-hydroxy-naphthalene-2-carboxylic acid or 3-hydroxynaphthalene-2-carboxylic acid; and sulfonic acids, such as ethanesulfonic acid, ethane-1,2-disulfonic acid, 2-hydroxyethane-sulfonic acid, methanesulfonic acid, (+)-camphor-10-sulfonic acid, benzenesulfonic acid, naph-thalene-2-sulfonic acid, naphthalene-1,5-disulfonic acid or p-toluenesulfonic acid. These salts may be prepared from compounds of formula (I) by known salt-forming procedures.

Compounds of formula (I) which contain acidic, e.g., carboxyl, groups, are also capable of forming salts with bases, in particular, pharmaceutically acceptable bases, such as those well-known in the art; suitable such salts include metal salts, particularly, alkali metal or alkaline earth metal salts, such as sodium, potassium, magnesium, calcium or zinc salts; or salts with ammonia or pharmaceutically acceptable organic amines or heterocyclic bases, such as benethamine, arginine, benzathine, diethanolamine, ethanolamine, 4(2-hydroxyethyl)morpholine, 1-(2-hydroxyethyl)pyrrolidine, N-methyl glucamine, piperazine, triethanol-amine or tromethamine. These salts may be prepared from compounds of formula (I) by known salt-forming procedures.

In those compounds where there is an asymmetric carbon atom or an axis of chirality the compounds exist in individual optically active isomeric forms or as mixtures thereof, e.g., as racemic or diastereomeric mixtures. The present invention embraces both individual optically active R and S isomers, as well as mixtures, e.g., racemic or diastereomeric mixtures, thereof.

Specific preferred compounds of formula (I) are described hereinafter in the Examples.

The invention also provides a process for the preparation of compounds of formula (I), in free or salt form, which comprises the steps of:
(i) (A) for the preparation of compounds of formula (I), wherein $R^6$ is H, cleaving the ester group —$COOR^6$ in a compound of formula (I),

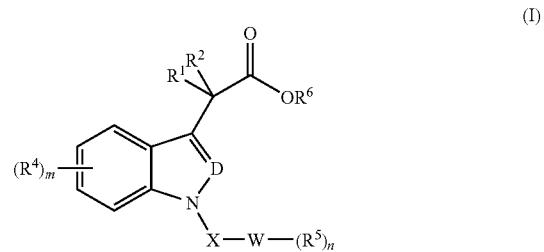

where $R^6$ is $C_1$-$C_8$-alkyl optionally substituted by $C_3$-$C_{15}$-carbocyclic group, or a $C_3$-$C_{15}$-carbocyclic group, and $R^1$, $R^2$, $R^4$, $R^5$, D, W, X, m, and n are as hereinbefore defined; or (B) for the preparation of compounds of formula (I), wherein $R^6$ is $C_1$-$C_8$-alkyl optionally substituted by $C_3$-$C_{15}$-carbocyclic group, or a $C_3$-$C_{15}$-carbocyclic group, reacting a compound of formula (II)

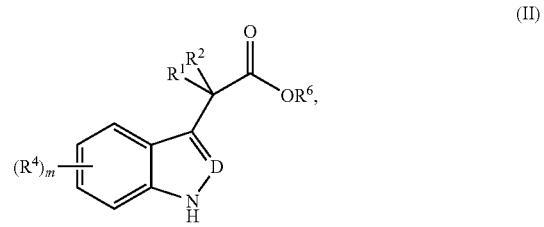

wherein
$R^6$ is $C_1$-$C_8$-alkyl optionally substituted by $C_3$-$C_{15}$-carbocyclic group or a $C_3$-$C_{15}$-carbocyclic group; and
$R^1$, $R^2$, $R^4$, D, and m are as hereinbefore defined with a compound of formula (III)

wherein
G is a leaving moiety, e.g., a halogen atom; and
$R^5$, W, X and n are as hereinbefore defined; and (ii) recovering the resultant compound of formula (I) in free or salt form.

Process variant (A) may be carried out using known methods (or analogously as hereinafter described in the Examples) for cleavage of carboxylic ester groups and can be carried out in situ after preparation of a compound of formula (I), where $R^6$ is $C_1$-$C_8$-alkyl optionally substituted by $C_3$-$C_{15}$-carbocyclic group, or a $C_3$-$C_{15}$-carbocyclic group. For example, the compound of formula (I), where $R^6$ is $C_1$-$C_8$-alkyl optionally substituted by $C_3$-$C_{15}$-carbocyclic group, or a $C_3$-$C_{15}$-carbocyclic group, which is conveniently in solution in a polar organic solvent or a mixture thereof with water, may be reacted with an aqueous inorganic base, such as NaOH or LiOH to hydrolyse the ester group; where the base is NaOH, the reaction may be carried out at a temperature of 10-40° C., conveniently ambient temperature, while when the base is LiOH the reaction may be started at −5° C. to 5° C. and then continued at 10-40° C., conveniently ambient temperature.

Process variant (B) may be carried out using known procedures or analogously as hereinafter described in the Examples. For example, the compound of formula (II) may be reacted with an alkyl halide of formula (III), where
G is halogen;
$R^5$, W, X and n are as hereinbefore defined, in the presence of an organic base, such as NaH; the reaction may be carried out in an organic solvent, e.g., a polar aprotic solvent, such as N,N-dimethylformamide (DMF) and may be carried out at 10-40° C., conveniently at ambient temperature.

Cleavage of carboxylic acid esters can be accomplished in situ when reacting a compound of formula (II) with a compound of formula (III) using DMSO and NaH. For example, in isolating a compound of formula (I), excess inorganic base, NaH, in the presence of adventitious water can generate the aqueous base NaOH, which can hydrolyse the compound of formula (I) to generate the carboxylic acid derivative as described under Process variant (A).

Compounds of formula (II) are known or may be obtained by known methods, e.g., as described in U.S. Pat. No. 3,320,268, or analogously as hereinafter described in the Examples. Compounds of formula (III) are known or may be obtained by known methods, or analogously, as hereinafter described in the Examples.

The compounds of formula (I) in free form may be converted into salt form, and vice versa, in a conventional manner. The compounds in free or salt form can be obtained in the form of hydrates or solvates containing a solvent used for crystallisation. Compounds of formula (I) can be recovered from reaction mixtures and purified in a conventional manner. Isomers, such as enantiomers, may be obtained in a conventional manner, e.g., by fractional crystallisation, chiral HPLC resolution or asymmetric synthesis from correspondingly asymmetrically substituted, e.g., optically active, starting materials.

Pharmaceutical Use and Assay

Compounds of formula (I) and their pharmaceutically acceptable salts, hereinafter referred to alternatively as "agents of the invention", are useful as pharmaceuticals. In particular, the compounds have good CRTh2 receptor modulator activity and may be tested in the following assays.

Filtration Binding Assay Protocol

The binding of CRTh2 modulators is determined using membranes prepared from human CRTh2-expressing Chinese Hamster Ovary cells (CHO.K1-CRTh2). To produce cell membranes CHO.K1-CRTh2 cells cultured in roller bottles are harvested using cell dissociation buffer (Invitrogen). The cells are pelleted by centrifugation (167 g, 5 min). The cell pellet is incubated in hypotonic buffer (15 mM Tris-OH, 2 mM $MgCl_2$, 0.3 mM EDTA, 1 mM EGTA, 1× Complete™ tablet) at 4° C. for 30 min. At 4° C. cells are homogenized using a Polytron® (IKA Ultra Turrax T25) for 5 bursts of 1 second. The homogenate is centrifuged (Beckman Optima™ TL Ultracentrifuge, 48000 g, 30 min at 4° C.). The supernatant is discarded and the membrane pellet resuspended in homogenisation buffer (75 mM Tris-OH, 12.5 mM MgCl2, 0.3 mM EDTA, 1 mM EGTA, 250 mM Sucrose, 1× Complete™ tablet. Membrane preparations are aliquoted and stored at 80° C. The protein content is estimated using Bradford Protein Assay Dye (Bio Rad).

The binding of $[^3H]$-$PGD_2$ (157 Ci/mmol) to CHO.K1-CRTh2 membranes is determined in the absence (total binding) and presence (non-specific binding) of unlabelled $PGD_2$ (1 µM). Subtraction of the cpm (counts per minute) of $[^3H]$-$PGD_2$ binding in presence of excess unlabelled $PGD_2$ from that observed in the absence of excess unlabelled $PGD_2$ is defined as specific binding. Active CRTh2 modulators are able to compete with $[^3H]$-$PGD_2$ for binding to the CRTh2 receptor and are identified in a decrease in the number of cpm bound.

The assay is performed in Greiner U-bottomed 96 well-plates, in a final volume of 100 µl per well. CHO.K1-CRTh2 membranes were diluted in assay buffer (10 mM HEPES-KOH (pH 7.4), 1 mM EDTA and 10 mM $MnCl_2$) and 10 µg are added to each well. $[^3H]$-$PGD_2$ is diluted in assay buffer and added to each well at a final concentration of 2.5 nM. To determine non-specific binding, $[^3H]$-$PGD_2$ binding to the CRTh2 receptor is competed with using unlabelled $PGD_2$ at a final well concentration of 1 µM. The experiment is done in triplicate, with reagents added to the wells as follows:

25 µL assay buffer for total binding or
25 µL $PGD_2$ to determine non-specific binding
25 µL $[^3H]PGD_2$
50 µL membranes
25 µL test compound in DMSO/assay buffer The plates are incubated at room temperature on a shaker for 1 hour, and then harvested (Tomtec Harvester 9600) onto GF/C filter plates using wash buffer (10 mM HEPES-KOH, pH 7.4). The plate is dried for 2 hours, prior to addition of Micro-Scint 20™ (50 µL) and sealing with TopSeal-S™. Plates are then counted using a Packard Top Count instrument, Plates are then read on the Packard Topcount with the 3H Scintillation program (1 min per well).

Ki (dissocation constant for the inhibition) values for the CRTh2 modulators are reported. Ki values are determined using Sigma Plot™ software, using the Cheng-Prussoff equation.

$$Ki=IC_{50}/1+[S]/Kd$$

where S is the concentration of radioligand and Kd is the dissociation constant.

CRTH2 cAMP Functional Assay Protocol

This assay is conducted in CHO.K1-CRTh2 cells. cAMP is generated in the cell by stimulating cells with 5 µM forskolin, an adenylate cyclase activator. $PGD_2$ is added to activate the CRTh2 receptor which results in the attenuation of the forskolin-induced cAMP accumulation. Potential CRTh2 antagonists are tested for their ability to inhibit the $PGD_2$-mediated attenuation of the forskolin-induced cAMP accumulation in CHO.K1-CRTh2 cells.

For each concentration value on the dose-response curve, test compounds are prepared in assay stimulation buffer (HBSS, 5 mM HEPES, 10 µM IBMX±0.1% human serum albumin) containing DMSO (3% vol/vol) and 5 µL/well is added to an assay plate (384 well white optiplate).

CHO.K1-CRTh2 cultured in tissue culture flasks are washed with PBS and harvested with dissociation buffer. Cells are washed with PBS and resuspended in stimulation buffer to a concentration of $0.4×10^6$/mL and added to the assay plate (10 µL/well).

The assay plate is incubated at room temperature on a shaker for 15 minutes.

A mix of agonist (10 nM Prostaglandin $D_2$) and 5 µM forskolin is prepared in assay stimulation buffer and added to the assay plate (5 µL/well).

In addition, a cAMP standard is serially diluted in assay stimulation buffer and added to separate empty wells on the assay plate (20 µL/well). The cAMP standard allows for the quantification of cAMP generated in CHO.K1-CRTH2 cells.

The assay plate is incubated at room temperature on a shaker for 60 minutes.

Cell lysis buffer (Lysis buffer: Milli-Q $H_2O$, 5 mM HEPES, 0.3% Tween-20, 0.1% human serum albumin) is added to a bead mix (containing Alphascreen™ anti-cAMP acceptor beads 0.06 units/µL, Alphascreen™ streptavidin-coated donor beads 0.06 units/µL, biotinylated cAMP 0.06 units/µL, 10 µM IBMX) is prepared under darkened conditions 60 minutes prior to addition to the assay plate. The resulting lysis mix is added to all wells of the assay plate (40 µL/well).

The assay plate is sealed with Topseal-S™ and incubated in the dark at room temperature on a shaker for 45 minutes. The plate is then counted using a Packard Fusion™ instrument.

The resulting counts per minute are converted to nM cAMP by using the prepared cAMP standard curve. $IC_{50}$ values (concentration of CRTh2 antagonist required to inhibit 50% of the $PGD_2$-mediated attenuation of forskolin-induced cAMP accumulation in CHO.K1-CRTh2 cells) are then determined using Prism™ software.

Compounds of the Examples herein below generally have Ki values in the SPA binding assay below 1 µM. For example, the compounds of Examples 2, 4, and 5 have Ki values of 0.008, 0.052, and 0.036 µM respectively.

Compounds of the Examples herein below generally have $IC_{50}$ values in the functional assay below 1 µM. For example, the compounds of Examples 2, 4, and 5 have $IC_{50}$ values of 0.073, 0.033, and 0.099 µM respectively.

Compounds of formula (I), in free or salt form, are modulators, of the G-protein-coupled chemoattractant receptor CRTh2, expressed on Th2 cells, eosinophils and basophils. $PGD_2$ is the natural ligand for CRTh2. Thus, modulators which inhibit the binding of CRTh2 and $PGD_2$ are useful in the treatment of allergic and anti-inflammatory conditions. Treatment in accordance with the invention may be symptomatic or prophylactic. "Modulators" as used herein is intended to encompass antagonists, agonists, partial antagonists and/or partial agonists. Preferably, modulators are antagonists. Accordingly, agents of the invention are useful in the treatment of inflammatory or obstructive airways diseases, resulting, e.g., in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitis asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., corticosteroid) or bronchodilatory. Prophylactic benefit in asthma may, in particular, be apparent in subjects prone to "morning dipping". "Morning dipping" is a recognised asthmatic syndrome, common to a substantial percentage of asthmatics and characterised by asthma attack, e.g., between the hours of about 4-6 a.m., i.e., at a time normally substantially distant from any previously administered symptomatic asthma therapy.

Other inflammatory or obstructive airways diseases and conditions to which the present invention is applicable include acute lung injury (ALI), adult respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis including, e.g., aluminosis, anthracosis, asbestosis, chalicosis, ptilosis, siderosis, silicosis, tabacosis and byssinosis.

Having regard to their anti-inflammatory activity, in particular, in relation to inhibition of eosinophil activation, agents of the invention are also useful in the treatment of eosinophil related disorders, e.g., eosinophilia, in particular, eosinophils-related disorders of the airways, e.g., involving morbid eosinophilic infiltration of pulmonary tissues including hypereosinophilia as it effects the airways and/or lungs, as well as, e.g., eosinophil-related disorders of the airways consequential or concomitant to Löffler's syndrome; eosinophilic pneumonia; parasitic, in particular, metazoan, infestation including tropical eosinophilia; bronchopulmonary aspergillosis; polyarteritis nodosa including Churg-Strauss syndrome; eosinophilic granuloma; and eosinophil-related disorders affecting the airways occasioned by drug-reaction.

Agents of the invention are also useful in the treatment of inflammatory or allergic conditions of the skin, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita and other inflammatory or allergic conditions of the skin.

Agents of the invention may also be used for the treatment of other diseases or conditions, in particular, diseases or conditions having an inflammatory component, e.g., treatment of diseases and conditions of the eye, such as conjunctivitis, keratoconjunctivitis sicca and vernal conjunctivitis; diseases affecting the nose including allergic rhinitis; and inflammatory disease, in which autoimmune reactions are implicated or having an autoimmune component or aetiology, including autoimmune hematological disorders, e.g., hemolytic anemia, aplastic anaemia, pure red cell anaemia and idiopathic thrombocytopenia; systemic lupus erythematosus; polychondritis; sclerodoma; Wegener granulamatosis; dermatomyositis; chronic active hepatitis; myasthenia gravis; Steven-Johnson syndrome; idiopathic sprue; autoimmune inflammatory bowel disease, e.g., ulcerative colitis and Crohn's disease; endocrine opthalmopathy; Grave's disease; sarcoidosis; alveolitis; chronic hypersensitivity pneumonitis; multiple sclerosis; primary billiary cirrhosis; uveitis (anterior and posterior); keratoconjunctivitis sicca and vernal keratoconjunctivitis; interstitial lung fibrosis; psoriatic arthritis; and glomerulonephritis, with and without nephrotic syndrome, e.g., including idiopathic nephrotic syndrome or minal change nephropathy.

Other diseases or conditions which may be treated with agents of the invention include septic shock; rheumatoid arthritis; osteoarthritis; proliferative diseases, such as cancer; mastocytosis, atherosclerosis; allograft rejection following transplantation; stroke; obesity; restenosis; diabetes, e.g., diabetes mellitus type I (juvenile diabetes) and diabetes mellitus type II; diarrhoeal diseases; ischemia/reperfusion injuries; retinopathy, such as diabetic retinopathy or hyperbaric oxygen-induced retinopathy; and conditions characterised by elevated intraocular pressure or secretion of ocular aqueous humor, such as glaucoma. Other diseases or conditions which may be treated with agents of the invention include neuropathic pain as described in WO 05/102338.

The effectiveness of an agent of the invention in inhibiting inflammatory conditions, e.g., in inflammatory airways diseases, may be demonstrated in an animal model, e.g., a mouse or rat model, of airways inflammation or other inflammatory conditions, e.g., as described by Szarka et al., *J Immunol Methods*, Vol. 202, pp. 49-57 (1997); Renzi et al., *Am Rev Respir Dis*, Vol. 148, pp. 932-939 (1993); Tsuyuki et al., *J Clin Invest*, Vol. 96, pp. 2924-2931 (1995); Cernadas et al., *Am J Respir Cell Mol Biol*, Vol. 20, pp. 1-8 (1999); and Williams and Galli, *J Exp Med*, Vol. 192, pp. 455-462 (2000).

The agents of the invention are also useful as co-therapeutic agents for use in combination with other drug substances, such as anti-inflammatory, bronchodilatory or antihistamine drug substances, particularly in the treatment of obstructive or inflammatory airways diseases, such as those mentioned hereinbefore, e.g., as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Such anti-inflammatory drugs include steroids, in particular, glucocorticosteroids, such as budesonide, beclamethasone dipropionate, fluticasone propionate, ciclesonide or mometasone furoate; or steroids, described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445 and WO 03/072592; non-steroidal glucocorticoid receptor agonists, such as those described in WO 00/00531, WO 02/10143, WO 03/082280, WO 03/082787, WO 03/104195 and WO 04/005229; LTB4 antagonists, such as those described in U.S. Pat. No. 5,451, 700; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID™ CC-10004 (Celgene), KW-4490 (Kyowa Hakko Kogyo), WO 03/104204, WO 03/104205, WO 04/000814, WO 04/000839 and WO 04/005258 (Merck), as well as those described in WO 98/18796 and WO 03/39544; A2a agonists, such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462 and WO 03/086408; A2b antagonists, such as those described in WO 02/42298; and beta (β)-2-adrenoceptor agonists, such as albuterol (salbutamol), metaproterenol, terbutaline, salmeterol, fenoterol, procaterol, and especially, formoterol and pharmaceutically acceptable salts thereof, and compounds (in free or salt or solvate form) of formula (I) of WO 00/75114, which document is incorporated herein by reference, preferably compounds of the Examples thereof, especially a compound of formula

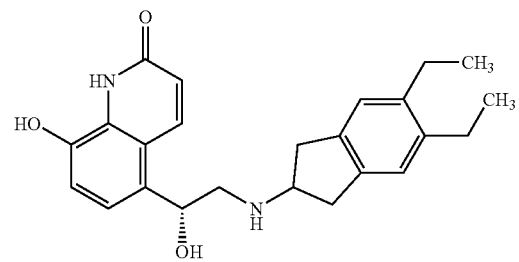

and pharmaceutically acceptable salts thereof, as well as compounds (in free or salt or solvate form) of formula (I) of WO 04/16601. Further β-2-adrenoreceptor agonists include compounds, such as those described in WO 99/64035, WO 01/42193, WO 01/83462, WO 02/066422, WO 02/070490, WO 02/076933, WO 2004/011416 and US 2002/0055651.

Such bronchodilatory drugs include anticholinergic or antimuscarinic agents, in particular, ipratropium bromide, oxitropium bromide, tiotropium salts and CHF 4226 (Chiesi), but also those described in WO 01/04118, WO 02/51841, WO 02/53564, WO 03/00840, WO 03/87094, WO 04/05285, WO 02/00652, WO 03/33495, WO 03/53966, EP 0424021, U.S. Pat. No. 5,171,744 and U.S. Pat. No. 3,714,357.

Such co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and steroids, β-2 agonists, PDE4 inhibitors or LTD4 antagonists may be used, e.g., in the treatment of COPD or, particularly, asthma. Combinations of agents of the invention and anticholinergic or antimuscarinic agents, PDE4 inhibitors, dopamine receptor agonists or LTB4 antagonists may be used, e.g., in the treatment of asthma or, particularly, COPD.

Other useful combinations of agents of the invention with anti-inflammatory drugs are those with antagonists of chemokine receptors, e.g., CCR-1, CCR-2, CCR-3, CCR-4, CCR-5, CCR-6, CCR-7, CCR-8, CCR-9, CCR-10, CXCR1, CXCR2, CXCR3, CXCR4 and CXCR5; particularly useful are CCR-3 antagonists, such as those described in WO 2002/026723, especially 4-{3-[(S)-4-(3,4-dichlorobenzyl)-morpholin-2-ylmethyl]-ureidomethyl}-benzamide and those described in WO 2003/077907, WO 2003/007939 and WO 2002/102775.

Also especially useful are CCR-5 antagonists, such as Schering-Plough antagonists SC-351125, SCH-55700 and SCH-D; Takeda antagonists, such as N-[[4-[[[6,7-dihydro-2-(4-methylphenyl)-5H-benzo-cyclohepten-8-yl]carbonyl] amino]phenyl]-methyl]tetrahydro-N,N-dimethyl-2H-pyran-4-aminium chloride (TAK-770); and CCR-5 antagonists, described in U.S. Pat. No. 6,166,037, WO 00/66558 and WO 00/66559.

The agents of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; or rectally, e.g., in the treatment of inflammatory bowel disease.

The present invention also provides a pharmaceutical composition comprising a compound of formula (I) in free form or in the form of a pharmaceutically acceptable salt, optionally together with a pharmaceutically acceptable diluent or carrier therefore. The composition may contain a co-therapeutic agent, such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight); and/or one or more surfactants, such as oleic acid or sorbitan trioleate; and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

The invention includes:
(a) an agent of the invention in inhalable form, e.g., in an aerosol or other atomizable composition or in inhalable particulate, e.g., micronised form;
(b) an inhalable medicament comprising an agent of the invention in inhalable form;
(c) a pharmaceutical product comprising such an agent of the invention in inhalable form in association with an inhalation device; and
(d) an inhalation device containing an agent of the invention in inhalable form.

Dosages of agents of the invention employed in practising the present invention will of course vary depending, e.g., on the particular condition to be treated, the effect desired and the mode of administration. In general, suitable daily dosages for oral administration are of the order of 0.01-100 mg/kg.

The invention is illustrated by the following Examples.

EXAMPLES

General Conditions

LCMS are recorded on an Agilent 1100 LC system with a Waters Xterra MS C18 4.6×100 5 μM column, eluting with 5-95% 10 mM aqueous ammonium bicarbonate in acetonitrile over 2.5 minutes, with negative ion electrospray ionization or 5-95% water+0.1% TFA in acetonitrile with positive ion electrospray ionization. $[M+H]^+$ refers to monoisotopic molecular weights.

| Abbreviations | |
|---|---|
| EtOH | ethanol |
| $CH_2Cl_2$ | dichloromethane |
| $MgSO_4$ | magnesium sulfate |
| aq | aqueous |
| DMF | N,N-dimethylformamide |
| EtOAc | ethyl acetate |
| HCl | hydrochloric acid |
| MeCN | acetonitrile |
| LiOH | lithium hydroxide |
| HPLC | high performance liquid chromatography |
| NaH | sodium hydride |
| $Et_2O$ | diethyl ether |
| $PBr_3$ | phosphorus tribromide |
| NaOH | sodium hydroxide |
| THF | tetrahydrofuran |
| DMSO | dimethyl sulfoxide |
| $Et_3N$ | triethylamine |
| MeOH | methanol |
| $H_2SO_4$ | sulfuric acid |

The following examples have been prepared using the process described herein.

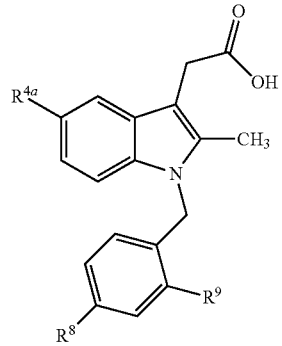

(Ia)

$R^{4a}$ = F except in Example 1 where $R^{4a}$ = H

| Example | $R^9$ | $R^8$ | $[M + H] +/ [M - H]^-$ |
|---|---|---|---|
| 1 | ![CF3 group with F substituents] | $SO_2CH_3$ | 426 |
| 2 | ![CF3 group with F substituents] | $SO_2CH_3$ | 444 |
| 3 | H | morpholinyl-$SO_2$ | 448 |

-continued (Ia)

[Structure: indole with R4a substituent, 2-methyl, 3-acetic acid, N-benzyl with R8, R9 substituents]

R4a = F except in Example 1 where R4a = H

| Example | R9 | R8 | [M + H] +/ [M − H]− |
|---------|----|----|---------------------|
| 4 | H | —S(O)₂—N(CH₃)(cyclohexyl) | 473 |
| 5 | H | —S(O)₂—N(pyrrolidinyl) | 431 |
| 6 | H | —S(O)₂—N(azetidinyl) | 417 |

Example 1

Preparation of [1-(4-methanesulfonyl-2-trifluoromethyl-benzyl)-2-methyl-1H-indol-3-yl]-acetic acid a) 4-Methanesulfonyl-2-trifluoromethyl-benzaldehyde

4-Methanesulfonyl-2-trifluoromethyl-benzaldehyde (50.0 g, 0.26 mol) is added to a suspension of sodium methanesulfinate (29.6 g, 0.29 mol) in DMSO (200 ml) at room temperature. The reaction mixture is heated at 90° C. for 16 h. The thick yellow suspension formed is poured into crushed ice-water (1 L) then filtered to afford an off-white powder.

b) (4-Methanesulfonyl-2-trifluoromethyl-phenyl)-methanol

To a suspension of 4-methanesulfonyl-2-trifluoromethyl-benzaldehyde (49.2 g, 0.20 mol) in dry EtOH (500 ml), cooled in an ice-bath, is added sodium borohydride (10.8 g, 0.22 mol), portionwise over 30 mins. The reaction mixture is allowed to warm up slowly to room temperature then stirring is continued for 16 h. The reaction mixture is poured into a beaker of crushed ice (700 ml) and adjusted to pH 1 with 2N HCl (approx. 200 ml). The resulting pale yellow suspension is extracted with CH$_2$Cl$_2$ (3×150 ml), dried (MgSO$_4$) and evaporated to dryness in vacuo. to afford a pale yellow solid.

c) 1-Bromomethyl-4-methanesulfonyl-2-trifluoromethyl-benzene

To a suspension of (4-methanesulfonyl-2-trifluoromethyl-phenyl)-methanol (50.3 g, 0.20 mol) in dry Et$_2$O (400 ml), cooled to 0° C., is added PBr$_3$ (6.5 ml, 0.07 mol) dropwise over 10 min. A sticky, thick yellow suspension forms which upon agitation and warming to room temperature changes to a fine white suspension. The reaction mixture is cooled again to 0° C. and water (200 ml) is added slowly. The suspension is neutralised at 10° C. with 4N NaOH aq (30 ml). The product is collected by filtration to give a white solid which is dried at 50° C. under high vacuum.

d) [1-(4-methanesulfonyl-2-trifluoromethyl-benzyl)-2-methyl-1H-indol-3-yl]-acetic acid methyl ester To a stirring solution of (2-methyl-1H-indol-3-yl)-acetic acid methyl ester (2.0 g, 10.5 mmol) in dry DMF (25 ml) at 0° C., is added portionwise NaH (0.46 g, 11.5 mmol) as a 60% dispersion in mineral oil. The reaction mixture is stirred at 0° C. for 1.5 h then NaI (1.72 g, 11.5 mmol) and 1-bromomethyl-4-methanesulfonyl-2-trifluoromethyl-benzene (3.65 g, 11.5 mmol) are added. The reaction mixture is stirred at room temperature for 16 h. The reaction mixture is poured into water (100 ml) and EtOAc (50 ml) is added. An emulsion is formed which is filtered. Brine (20 ml) is added to the filtrate and the organic phase is separated and dried (MgSO$_4$). Evaporation in vacuo affords a brown oil. Purification by flash chromatography on silica gel using 5:1 iso-hexane:EtOAc, increasing polarity up to 3:1 iso-hexane:EtOAc, gives the desired product; [M+H]+ 440.

e) [1-(4-methanesulfonyl-2-trifluoromethyl-benzyl)-2-methyl-1H-indol-3-yl]-acetic acid To a stirring solution of [1-(4-methanesulfonyl-2-trifluoromethyl-benzyl)-2-methyl-1H-indol-3-yl]-acetic acid methyl ester (440 mg, 1.0 mmol) in 1:1 THF:MeOH (20 ml) at room temperature, is added 1N NaOH aq (5 ml). The reaction mixture is stirred at room temperature for 16 h. The reaction mixture is evaporated in vacuo, diluted with water (10 ml) and acidified to acidic pH with 6N HCl aq. The precipitated product is collected by filtration and recrystallised from 1:3 isopropyl alcohol:water. The product is dried under high vacuum at 50° C.; [M+H]+ 426.

Example 2

Preparation of [5-fluoro-(4-methanesulfonyl-2-trifluoromethyl-benzyl)-2-methyl-1H-indol-3-yl]-acetic acid a) (5-fluoro-2-methyl-1H-indol-3-yl)-acetic acid ethyl ester

Using the procedure reported in U.S. Pat. No. 4,302,589:
To a suspension of commercially-available 4-fluorophenylhydrazine hydrochloride (12.34 g, 78.5 mmol) and levulinic acid (7.70 ml, 75.0 mmol) EtOH (95 ml), is added conc. H$_2$SO$_4$ (7.5 ml). The reaction mixture is heated at reflux under argon for 22 h. The reaction mixture is poured into ice-water (200 ml) then extracted with dichloromethane (100 ml). The organic phase is washed with brine (100 ml), dried (MgSO$_4$) and concentrated in vacuo. The resulting brown oil is purified by column chromatography on silica gel eluting with iso-hexane/EtOAc (6:1) to afford a light brown solid. Trituration with iso-hexane (4×2 ml) gives the title compound as a pale yellow solid; [M+H]$^+$ 235.

b) [5-fluoro-(4-methanesulfonyl-2-trifluoromethyl-benzyl)-2-methyl-1H-indol-3-yl]-acetic acid ethyl ester To a stirring solution of (5-fluoro-2-methyl-1H-indol-3-yl)-acetic acid ethyl ester (100 mg, 0.43 mmol) in dry DMSO (2 ml) at room temperature, is added sodium hydride (26 mg, 0.65 mmol) as a 60% dispersion in mineral oil. After stirring at room temperature for 30 mins, 1-bromomethyl-4-methanesulfonyl-2-trifluoromethyl-benzene (216 mg, 0.68 mmol) (intermediate 1c) and sodium iodide (102 mg, 0.68 mmol) are added. The reaction mixture is stirred at room temperature for 60 h. The reaction mixture is poured into water (20 ml) and extracted with EtOAc (20 ml). The organic phase is dried (MgSO$_4$) and evaporated to dryness in vacuo. The crude product is purified by reverse phase chromatography on a C18 Isolute™ cartridge, eluting in 0-100% MeCN in water, using a FlashMaster Personal™ and GradMaster™; [M+H]+ 472.

c) [5-fluoro-(4-methanesulfonyl-2-trifluoromethyl-benzyl)-2-methyl-1H-indol-3-yl]-acetic acid To a stirring solution of [5-fluoro-(4-methanesulfonyl-2-trifluoromethyl-benzyl)-2-methyl-1H-indol-3-yl]-acetic acid ethyl ester (28 mg, 0.06 mmol) dissolved in THF (1 ml) at room temperature, is added 2N LiOH aq (1 ml). The reaction mixture is stirred at room temperature for 2 h and partitioned between water/EtOAc (20 ml). The aqueous phase is separated and acidified with 1N HCl aq to pH 4. The product is extracted into EtOAc (20 ml), dried (MgSO$_4$) and evaporated in vacuo; [M+H]+ 444.

Example 3

Preparation of {5-Fluoro-2-methyl-1-[4-(morpholine-4-sulfonyl)-benzyl]-1H-indol-3-yl}-acetic acid a) 4-(4-bromomethyl-benzenesulfonyl)-morpholine To a stirring solution of commercially-available 4-bromomethyl benzenesulfonyl chloride (1.0 g, 3.71 mmol) in dichloromethane (8 ml) at 0° C. under an argon atmosphere, is added triethylamine (0.575 ml, 4.1 mmol), in one portion, followed by morpholine (0.359 ml, 4.1 mmol). The reaction mixture is stirred for 20 h, warming up slowly to room temperature. The reaction mixture is then diluted with 2N HCl aq (40 ml) and extracted in dichloromethane (20 ml), dried (MgSO$_4$) and evaporated to dryness in vacuo to afford the title compound. No mass ion detected.

b) {5-Fluoro-2-methyl-1-[4-(morpholine-4-sulfonyl)-benzyl]-1H-indol-3-yl}-acetic acid To a stirring suspension of (5-fluoro-2-methyl-1H-indol-3-yl)-acetic acid ethyl ester (100 mg, 0.43 mmol) in dry DMSO (1 ml), is added NaH (29 mg, 0.73 mmol). The reaction mixture is stirred at room temperature for 15 min after which time 4-(4-bromomethyl-benzenesulfonyl)-morpholine (136 mg, 0.43 mmol) is added. The reaction mixture is diluted with water (2 ml) and treated with 1N HCl aq to acidic pH. The crude reaction mixture is purified by reverse phase chromatography on a C18 Isolute™ cartridge (70 g) eluting in 0-100% MeCN in water using a FlashMaster Personal™ and GradMaster™; [M+H]+ 448.

Example 4

Preparation of {1-[4-(Cyclohexyl-methyl-sulfamoyl)-benzyl]-5-fluoro-2-methyl-1H-indol-3-yl}-acetic acid a) 4-Bromomethyl-N-cyclohexyl-N-methyl-benzene-sulfonamide The title compound is prepared analogously to Example 3a by replacing morpholine with N-methylcyclohexylamine to give 4-bromomethyl-N-cyclohexyl-N-methyl-benzenesulfonamide; no mass ion detected.

b) {1-[4-(Cyclohexyl-methyl-sulfamoyl)-benzyl]-5-fluoro-2-methyl-1H-indol-3-yl}-acetic acid To a stirring suspension of (5-fluoro-2-methyl-1H-indol-3-yl)-acetic acid ethyl ester (100 mg, 0.43 mmol) in dry DMSO (1 ml), is added NaH (29 mg, 0.73 mmol). The reaction mixture is stirred at room temperature for 15 min after which time 4-bromomethyl-N-cyclohexyl-N-methyl-benzenesulfonamide (149 mg, 0.43 mmol) is added. Reaction mixture is diluted with water (10 ml) and treated with 1N HCl aq to acidic pH. The product is extracted in 1:1 EtOAc:Et$_2$O (20 ml), washed with brine, dried (MgSO$_4$) and evaporated in vacuo. The crude reaction mixture is purified by preparative MS-directed HPLC to afford the title compound; [M+H]+ 474.

Example 5

Preparation of {5-Fluoro-2-methyl-1-[4-(pyrrolidine-1-sulfonyl)-benzyl]-1H-indol-3-yl}-acetic acid The title compound is prepared analogously to Example 4 by replacing N-methylcyclohexylamine with pyrrolidine to give {5-Fluoro-2-methyl-1-[4-(pyrrolidine-1-sulfonyl)-benzyl]-1H-indol-3-yl}-acetic acid; [M+H]+ 431.

Example 6

Preparation of {1-[4-(Azetidine-1-sulfonyl)-benzyl]-5-fluoro-2-methyl-1H-indol-3-yl}-acetic acid The title compound is prepared analogously to Example 4 by replacing N-methylcyclohexylamine with azetidine to give {1-[4-(Azetidine-1-sulfonyl)-benzyl]-5-fluoro-2-methyl-1H-indol-3-yl}-acetic acid; [M+H]$^+$ 417.

What is claimed is:

1. A compound of formula (Ia):

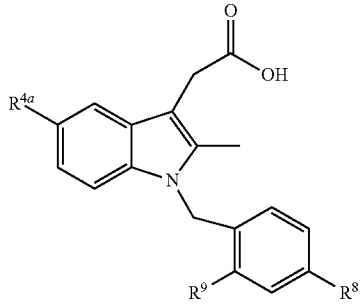

where
$R^{4a}$ is H or fluorine;
$R^9$ is H or $C_1$-$C_8$-haloalkyl, and when $R^8$ is —$SO_2$—$C_1$-$C_8$-alkyl, $R^9$ is $C_1$-$C_8$-haloalkyl; and $R^8$ is selected from —$SO_2$—$C_1$-$C_8$-alkyl,

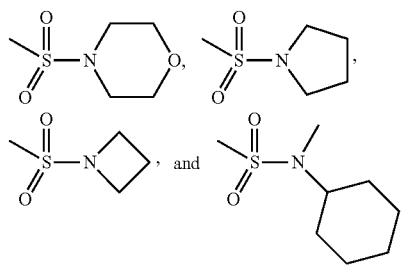

or a pharmaceutically acceptable salt thereof.

2. A pharmaceutical composition comprising:
a compound according to claim 1 and a pharmaceutically acceptable diluent or carrier.

* * * * *